United States Patent [19]

Powlan

[11] Patent Number: 4,823,782
[45] Date of Patent: Apr. 25, 1989

[54] LEG SLING

[76] Inventor: Roy Y. Powlan, 1 Chapel Dr., Lafayette, Calif. 94549

[21] Appl. No.: 688,075

[22] Filed: Dec. 31, 1984

[51] Int. Cl.⁴ .............................................. A61F 5/40
[52] U.S. Cl. ................................................... 128/94
[58] Field of Search .......................................... 128/94

[56] References Cited

U.S. PATENT DOCUMENTS

| 1,269,734 | 6/1918 | Noland | 128/94 |
| 2,088,927 | 8/1937 | Roy | 128/94 |
| 3,583,398 | 8/1968 | Bailey | 128/94 |

*Primary Examiner*—Gene Mancene
*Assistant Examiner*—Wenceslao J. Contreras

[57] ABSTRACT

A sling for supporting the limb of a patient is formed of a panel of fabric that is foreshortened along a given axis and is supported by suspending it by means engaging the panel at its four corners.

6 Claims, 1 Drawing Sheet

U.S. Patent        Apr. 25, 1989        4,823,782

LEG SLING

The invention relates to slings for supporting human limbs and, more particularly, to a sling for supporting the leg in a comfortable, flexed position during a therapeutic convalescence.

Treatment of the leg for fractures and other injuries often requires medical procedures that immobilize the leg of the patient for extended periods of time. In such cases, the leg must be suspended with the knee slightly bent in a flexed position. Heretofore, the suspension of the leg has been customarily accomplished by the use of a band of cloth or canvas passed under and behind the patient's knee and suspended from a point above the knee so as to form a sling for the leg. This type of sling is very unsatisfactory as the cloth or canvas band bunches up under the knee in a very short time causing the patient much discomfort and cutting off circulation of blood to the leg.

The present invention has for its object the provision of a simple sling that will not have the drawbacks of the prior art.

Another object of the invention is to provide a sling for supporting the leg of a patient in a comfortable, flexed position for an extended period of time without causing the patient discomfort or interferring with the patient's circulation of blood.

Figure 1:
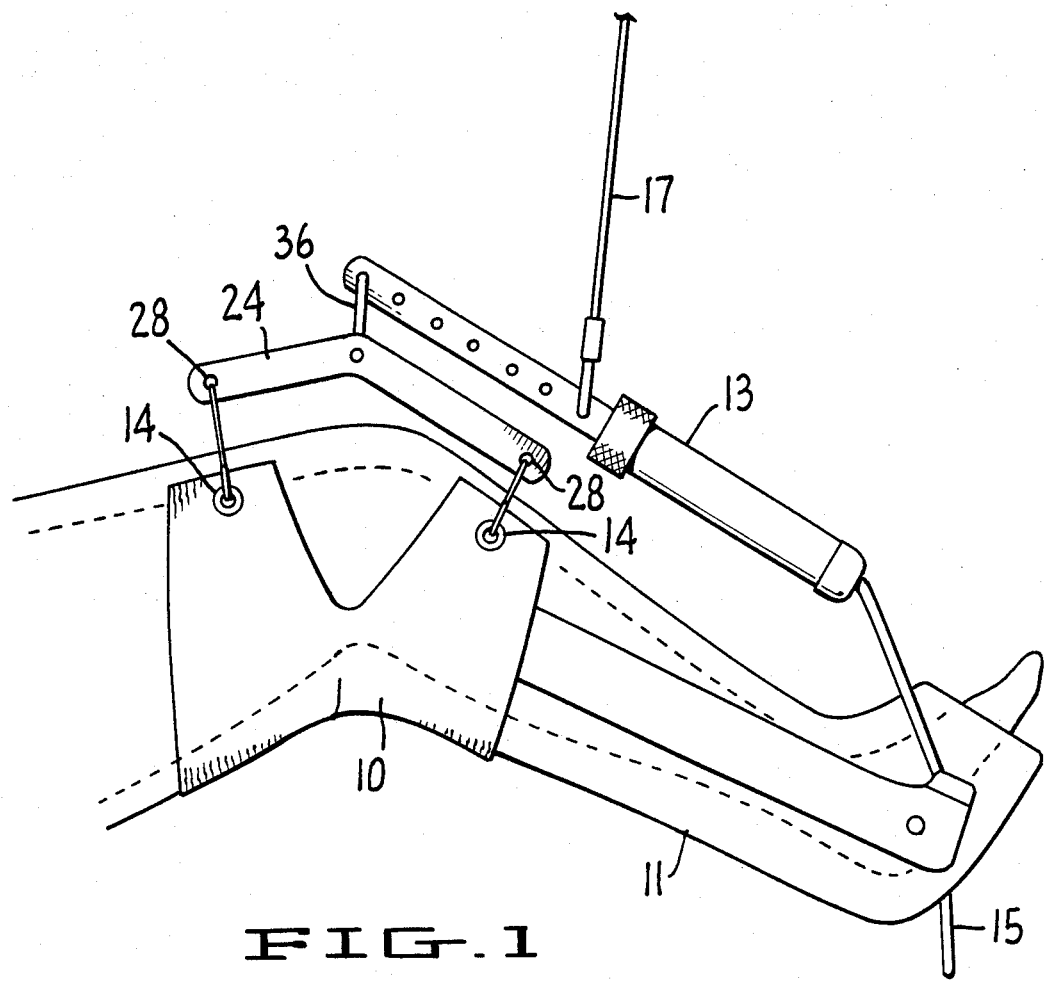
Figure 2:
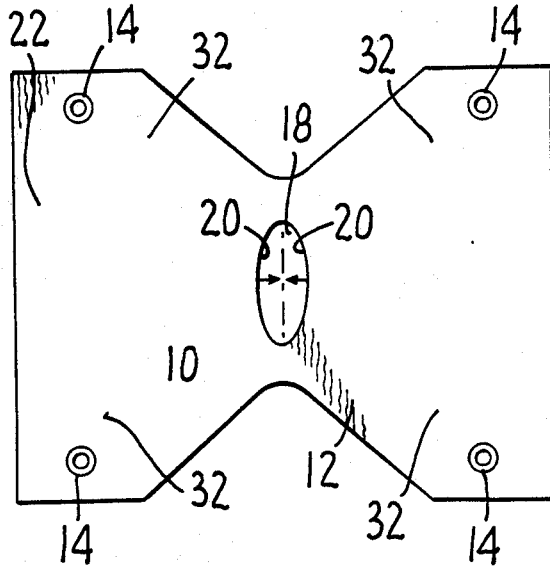
Figure 3:
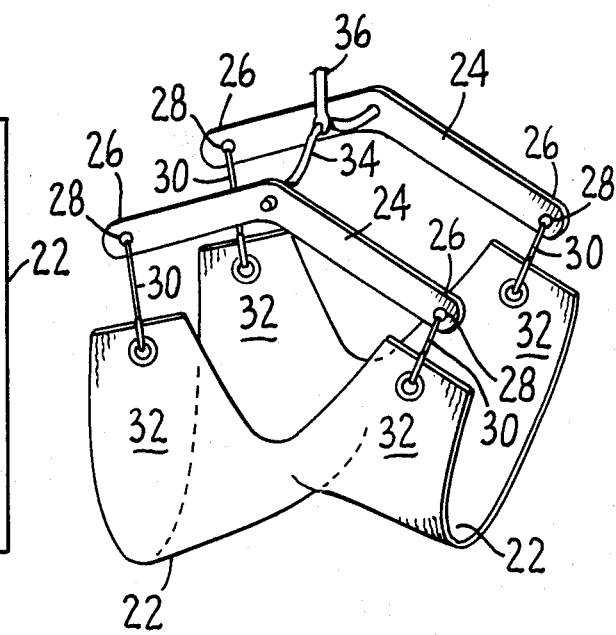

In the accompanying drawings, in which similar reference numerals refer to similar parts, FIG. 1 is a side elevation view of the invention showing its application to a leg under traction, FIG. 2 is a plan view of the fabric panel of applicant's sling before application to a patient, and FIG. 3 is a perspective view of the sling and a preferred form of suspension apparatus therefor.

The applicant's sling is particularly suited for suspending a leg in traction. As is shown in FIG. 1, the patient's leg is placed in a plastic foam traction boot 11. A traction device, such as that shown and described in applicant's copending application Ser. No. 543,857, is provided to exert a constant pull on the patient's leg and the device shown includes a vector bar 13 that rests upon a foot stand 15 and is suspended from the cable 17. For the patient's confort, the leg, in such situations, must be suspended in a position slightly flexed at the knee. In this position, the lower thigh above the knee and the upper calf below the knee are disposed at oppositely inclined angles from each other with the result that any band of cloth or canvas placed under the leg adjacaent the knee tends to ride up, and bunch up, behind the knee.

The applicant's sling 10 is so constructed and suspended as to effectively counter these tendencies. As seen in FIG. 2, the applicant's sling 10 is formed from a substantially rectangular panel 12 of cloth or canvas. Two pairs of oppositely disposed grommets 14,14 or other fastening means are located adjacent the four corners of the panel and two triangular cutouts in the panel 12 are made intermediate the ends 22,22. A football-shaped, eliptical cut-out 18 is also made midway between the ends of the panel 12 and the edges 20,20 of this cutout are then sewn together. This modification of the panel 12 has the effect of shortening it along a central axis and disposing the opposite end portions 22,22 of the panel in approximately the same inclination as the patient's lower thigh and upper calf when the knee is slightly flexed.

Suspension of the sling 10 is preferably effected through the use of a pair of substantially parallel suspension arms 24,24. Each of the arms 24,24 is slghtly bent so as to roughly conform to the curavature of the patient's leg at the knee and the arms are long enough that the ends 26,26 thereof extend above and below the patient's knee joint. At each end of the arms an opening 28,28 is provided for a hook 30,30 that connects the opening 28,28 in the arm 24,24 with the adjacent grommet 14,14 in the sling 10. This arrangement causes the sides 32,32 and ends 22,22 of the sling to fit around the patient's leg at the knee to form a cradle that supports the leg. A central yoke 34 interconnects the suspension arms 24,24 adjacent their midpoints and the yoke carries a primary suspension hook 36 that suspends the sling 10 and the suspension arms 24,24 from the vector bar 13 of the traction device.

This sling and suspension arrangement provides a means of supporting the patient's leg in a comfortble, flexed position without any tendency on the part of the sling to ride up or bunch up behind the patient's knee. The reason for this is that the supporting forces on the sling are applied at points 14,14 above and below the patient's knee joint and are directed by the suspension arms 24,24 outwardly away from the patient's knee. The fashioning of the sling panel 12 in the same approximate inclination as the patient's leg also aids in eliminating any tenency of the sling to bunch up behind the knee.

I claim:

1. A sling for supporting the leg of a patient at the knee, said sling comprising:
   (a) a substantially rectangular fabric panel having two pairs of fastening means disposed adjacent the corners of the panel,
   (b) said panel being foreshortened along a central axis, and
   (c) means for suspending said panel by said fastening means, one pair of said fastening means being suspended from a point below the patient's knee and the other of said pair of fastening means being suspended from a point above the patient's knee.

2. A sling for supporting the leg of a patient as set forth in claim 1 wherein the foreshortening of the panel is done midway between the ends of the fabric panel.

3. A sling for supporting the leg of a patient as set forth in claim 2 wherein said two pairs of fastening means are disposed at opposite ends of the fabric panel.

4. A sling for supporting the leg of a patient as set forth in claim 3 wherein said suspension means comprise a pair of substantially parallel arms positioned above the patient's knee.

5. A sling for supporting the leg of a patient as set forth in claim 4 wherein said arms extend above and below the patient's knee.

6. A sling for supporting the leg of a patient at the knee, said sling comprising:
   (a) a substantially rectangular fabric panel having two pairs of openings disposed adjacent the corners of the panel,
   (b) said panel being foreshortened along a central axis at a point midway between the ends of the panel,
   (c) said panel also having substantially triangular cutouts taken from each side of the panel midway between the ends,
   (d) a pair of substantially parallel arms disposed above the patient's knee, each of said arms extending above and below the knee and having openings in the ends thereof, (e) hooks connecting the openings in the fabric panel with the openings in the parallel arms to suspend the panel from a point above the knee and from a point below the knee in a cradle underneath and behind the patient's knee, (f) means interconnecting the parallel arms, and (g) means for suspending the arms and the fabric panel by said interconnection means.

* * * * *